United States Patent
Taguchi

(10) Patent No.: US 9,324,751 B2
(45) Date of Patent: Apr. 26, 2016

(54) IMAGE SENSOR, PRODUCTION METHOD THEREFOR, AND INSPECTION APPARATUS

(75) Inventor: Ayumu Taguchi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 138 days.

(21) Appl. No.: 14/127,221

(22) PCT Filed: Aug. 1, 2012

(86) PCT No.: PCT/JP2012/004883
§ 371 (c)(1),
(2), (4) Date: Dec. 18, 2013

(87) PCT Pub. No.: WO2013/027338
PCT Pub. Date: Feb. 28, 2013

(65) Prior Publication Data
US 2014/0118590 A1    May 1, 2014

(30) Foreign Application Priority Data
Aug. 24, 2011   (JP) .................................. 2011-182131

(51) Int. Cl.
*H01L 27/146*   (2006.01)
*H04N 5/359*   (2011.01)
*H01L 27/14*   (2006.01)
*G01N 21/64*   (2006.01)

(52) U.S. Cl.
CPC ...... *H01L 27/14623* (2013.01); *G01N 21/6454* (2013.01); *H01L 27/14* (2013.01); *H01L27/1463* (2013.01); *H01L 27/14627* (2013.01); *H04N 5/359* (2013.01); *H01L 27/14685* (2013.01)

(58) Field of Classification Search
CPC .. H04N 5/359; H01L 27/14; H01L 27/14685; G01N 21/6454
See application file for complete search history.

(56) References Cited

U.S. PATENT DOCUMENTS

| | | | |
|---|---|---|---|
| 2003/0001122 A1 | 1/2003 | Shimizu et al. | |
| 2006/0014151 A1* | 1/2006 | Ogura et al. | 435/6 |
| 2007/0281315 A1* | 12/2007 | Takahashi et al. | 435/6 |

FOREIGN PATENT DOCUMENTS

| | | |
|---|---|---|
| JP | 2003-042954 | 2/2003 |
| JP | 2006-004991 | 1/2006 |
| JP | 2009-180740 | 8/2009 |

OTHER PUBLICATIONS

International Search Report; Application No. PCT/JP2012/004883; Filed: Aug. 1, 2012. Completion of International Search Report: Sep. 5, 2012. (Form PCT/ISA/210).

*Primary Examiner* — Jason Flohre
(74) *Attorney, Agent, or Firm* — Michael Best & Friedrich LLP

(57) ABSTRACT

[Object]
To provide an image sensor having high light collection efficiency and less crosstalk among pixels, a production method therefor, and an inspection apparatus.
[Solving means]
In an image sensor including a light source conversion unit that includes a plurality of light-receiving devices and converts incident light into an electric signal, a plurality of lenses that are provided in an immediately-above area of the light-receiving devices and collect light toward a light-receiving unit of the light-receiving devices positioned right below the lenses, and an insulation layer that is formed of an optically-transparent material and formed above the lenses, detection areas are provided on a surface of the insulation layer while being apart from one another for each of the light-receiving devices, a center of each of the detection areas being positioned on an extended line connecting a center of the light-receiving unit of each of the light-receiving devices and a center of the lens provided right above each of the light-receiving devices. In addition, a sample as a detection target is fixed to at least the detection areas.

20 Claims, 9 Drawing Sheets

1:Pixel cell 2:Detection area 3:Photoelectric conversion unit
4 Light-receiving unit 5:Macro-lens 6:Insulation layer
11:Sample 1:Pixel cell 2:Detection area 10:Image sensor 1:Pixel cell 2:Detection area 3:Photoelectric conversion unit
4 Light-receiving unit 5:Macro-lens 6:Insulation layer
11:Sample (a)

(b)

4, 104:Light-receiving unit  5, 105:Macro-lens
6, 106:Insulation layer  11:Sample  13:Fluorescent light (a)

(b)

4, 104:Light-receiving unit  5, 105:Macro-lens  6, 106:Insulation layer
11:Sample  13:Fluorescent light  14, 114:Imaging surface  107:Light-receiving device
115 Adjacent pixel stroke 4:Light-receiving unit 5:Macro-lens 6:Insulation layer
11:Sample 13:Fluorescent light 4:Light-receiving unit 5:Macro-lens 6:Insulation layer
11a to 11c:Sample 12:Excitation light 13:Fluorescent light 11a to 11c:Sample 12:Excitation light 13:Fluorescent light
104:Light-receiving unit 105:Macro-lens 106:Insulation layer 1:Pixel cell 2:Detection area 3:Photoelectric conversion unit
4 Light-receiving unit 5:Macro-lens 6:Insulation layer
11:Sample 22:Light shield mask

IMAGE SENSOR, PRODUCTION METHOD THEREFOR, AND INSPECTION APPARATUS

TECHNICAL FIELD

The present disclosure relates to an image sensor including a light collection structure, a production method therefor, and an inspection apparatus, more specifically, to an image sensor that detects a luminescence process of a sample, a production method therefor, and an inspection apparatus.

BACKGROUND ART

In a biological science field, there is an analytical method of concurrently detecting a minute luminescence process for a large number of samples. For example, when wishing to fix proteins included in a solution, an ELISA method (Enzyme Linked Immuno Sorbent Assay method) or the like has been used from the past. The ELISA method is a measurement method involving immersing a substrate on which a large number of antibodies are arranged/fixed into a solution including proteins as a measurement target, exposing it to antibodies that have undergone fluorescence modification after that, and exposing it to excitation light to observe it with a microscope. With such a method, which antibody reacted with respect to what fluorescence position can be judged.

On the other hand, most of the light generated in the luminescence process starting with fluorescent light is radiated isotropically in a peripheral space. Therefore, in the method that uses a microscope for observing a luminescence process as in the ELISA method or the like described above, there is a problem that detection efficiency is limited due to light collection efficiency of a microscope, and thus a favorable result cannot be obtained.

As a method of improving the detection efficiency in a luminescence process, a light-receiving device may be provided in the vicinity of a luminescence source (sample). For example, if a luminescence process of a detection target is caused in a fairly-small space, a CMOS (Complementary Metal Oxide Semiconductor) or CCD (Charge Coupled Device) image sensor can be used.

In this case, by structuring a light detection system in a form in which a unit pixel of an image sensor corresponds to one luminescence process, luminescence processes of a million unit can concurrently be recorded and analyzed in time series. Moreover, with a structure in which the luminescence processes appear in the vicinity of a surface of the image sensor, the concurrent luminescence processes of a large number of samples can be measured with a compact detection system.

From the reasons as described above, there is proposed an image sensor for measuring body tissues such as a cell (see, for example, Patent Documents 1 and 2). For example, in the image sensor disclosed in Patent Document 1, for improving detection accuracy, an optical filter layer that transmits a fluorescence wavelength range as well as block an excitation light wavelength range is provided on an upper surface of a photodiode of each pixel cell.

On the other hand, in the image sensor disclosed in Patent Document 2, a detection sensitivity is improved by forming an antireflection film on a light-receiving surface and improving a transmission on the light-receiving surface. Moreover, in the image sensor disclosed in Patent Document 2, a spot where a large number of biological macromolecules such as a single-strand probe DNA are gathered is formed in a matrix on the antireflection film, and a specific sample is coupled to the spot.

CITATION LIST

Patent Document

Patent Document 1: Japanese Patent Application Laid-open No. 2005-227155
Patent Document 2: Japanese Patent Application Laid-open No. 2006-30162

SUMMARY

Technical Problem

However, the image sensors of the related art described above have a problem that crosstalk occurs among adjacent pixels. For example, when a luminescence process occurs in the vicinity of a sensor surface, light emitted from a sample is emitted isotropically as described above, with the result that not only the pixels right below, but also the pixels in the vicinity are also affected. Therefore, in the image sensors of the related art, the luminescence process cannot be detected independently for each pixel, and thus the number of luminescence processes that can be detected is inevitably limited.

As a method of reducing crosstalk among pixels, a light shield wall may be provided among the pixels of the image sensors, but since the production steps become complex in such a case, a perfect light shield wall is currently not formed in the image sensors of the related art.

In this regard, the present disclosure mainly aims at providing an image sensor that has high light collection efficiency and less crosstalk among pixels, a production method therefor, and an inspection apparatus.

Solution to Problem

According to the present disclosure, there is provided an image sensor, including: a light source conversion unit that includes a plurality of light-receiving devices and converts incident light into an electric signal; a plurality of lenses that are provided in an immediately-above area of the light-receiving devices and collect light toward a light-receiving unit of the light-receiving devices positioned right below the lenses; an insulation layer that is formed of an optically-transparent material and formed above the lenses; and detection areas that are provided on a surface of the insulation layer while being apart from one another for each of the light-receiving devices, a center of each of the detection areas being positioned on an extended line connecting a center of the light-receiving unit of each of the light-receiving devices and a center of the lens provided right above each of the light-receiving devices, a sample as a detection target being fixed to at least the detection areas.

In the image sensor, when a refractive index of the insulation layer is represented by n and a distance between the sample and the lens is represented by L, a focal distance f of the lens may be shorter than an optical path length (=n*L) between the sample and the lens.

Further, the sample as the detection target may be fixed to only the detection areas. In this case, the detection areas may be subjected to surface processing or an antibody, an adapter, or a gene-adsorptive material may be fixed thereto.

Further, the surface of the insulation layer may have a light shield mask formed on a portion excluding the detection areas.

Furthermore, the insulation layer may be formed of silicon oxide.

According to the present disclosure, there is provided a production method for an image sensor, including the steps of: forming, on a semiconductor wafer, a photoelectric conversion unit that includes a plurality of light-receiving devices and converts incident light into an electric signal; forming, in an immediately-above area of the light-receiving devices, a plurality of lenses that collect light toward a light-receiving unit of the light-receiving devices positioned right below the lenses; forming, above the lenses, an insulation layer that is formed of an optically-transparent material; and forming, on a surface of the insulation layer while being apart from one another for each of the light-receiving devices, detection areas whose center is positioned on an extended line connecting a center of the light-receiving unit of each of the light-receiving devices and a center of the lens provided right above each of the light-receiving devices.

According to the present disclosure, there is provided an inspection apparatus including the image sensor described above.

Effects of Invention

According to the present disclosure, since the detection areas are provided in the immediately-above area of the center portion of the light-receiving devices on the surface of the insulation layer, light collection efficiency can be improved, and crosstalk among pixels can be reduced.

BRIEF DESCRIPTION OF DRAWINGS

FIG. 1 is a plan view schematically showing a structure of an image sensor according to a first embodiment of the present disclosure.

FIG. 2 is a cross-sectional diagram showing a structure of a pixel cell 1 shown in FIG. 1.

FIG. 3(a) is a diagram showing a light collection state in the image sensor 10 of this embodiment,
and FIG. 3(b) is a diagram showing a light collection state of an image sensor of the related art.

FIG. 4(a) is a diagram showing a focal point formation of a macro-lens 5,
and FIG. 4(b) is a diagram showing a state when measured by the image sensor of the related art.

FIG. 5 is a diagram showing a favorable condition of a focal distance f of the macro-lens 5.

FIG. 6 is a diagram schematically showing a measurement state of the image sensor 10 shown in FIG. 1.

FIG. 7 is a diagram schematically showing a measurement state when a detection area is not limited to a center portion of a pixel.

FIG. 8 is a cross-sectional diagram showing a structure of a pixel cell of an image sensor according to a second embodiment of the present disclosure.

FIG. 9 is a block diagram showing a structure of an inspection apparatus according to a third embodiment of the present disclosure.

DESCRIPTION OF EMBODIMENTS

Hereinafter, embodiments of the present disclosure will be described with reference to the attached drawings.

It should be noted that the present disclosure is not limited to the following embodiments. Further, descriptions will be given in the following order.

1. First Embodiment
   (Example of image sensor in which sample is fixed to only pixel center portion)
2. Second Embodiment
   (Example of image sensor in which light shield mask is provided in portion excluding detection area)
3. Third Embodiment
   (Example of inspection apparatus on which image sensor is mounted)

<1. First Embodiment>

Figure 1:
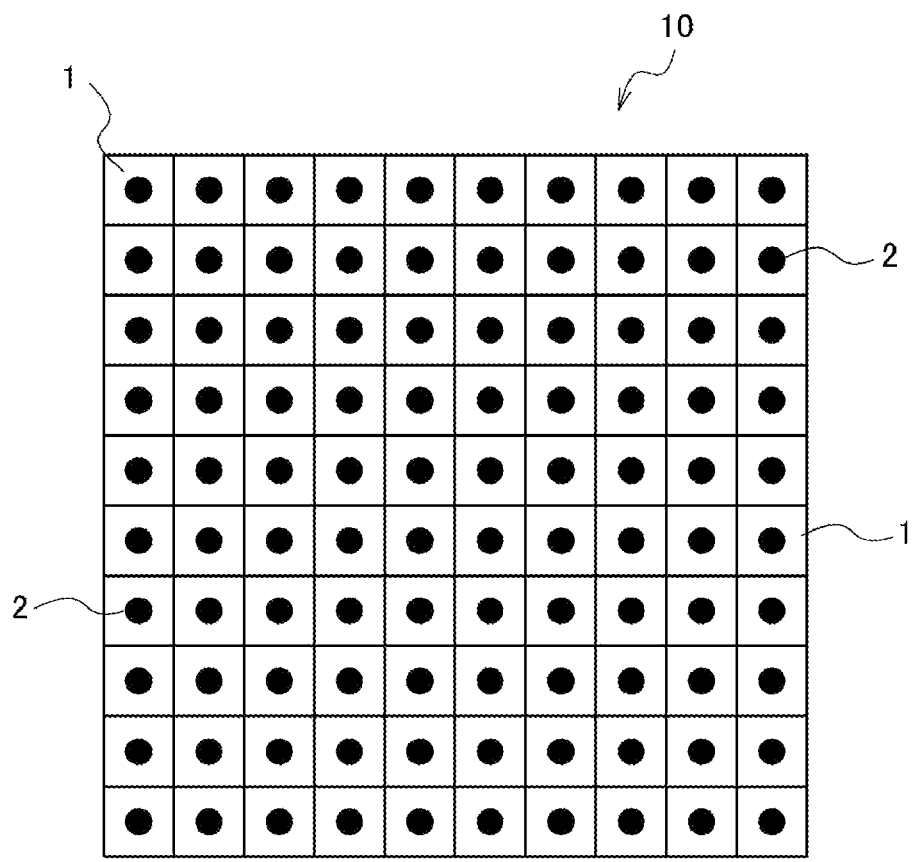
[FIG. 1]
Figure 2:
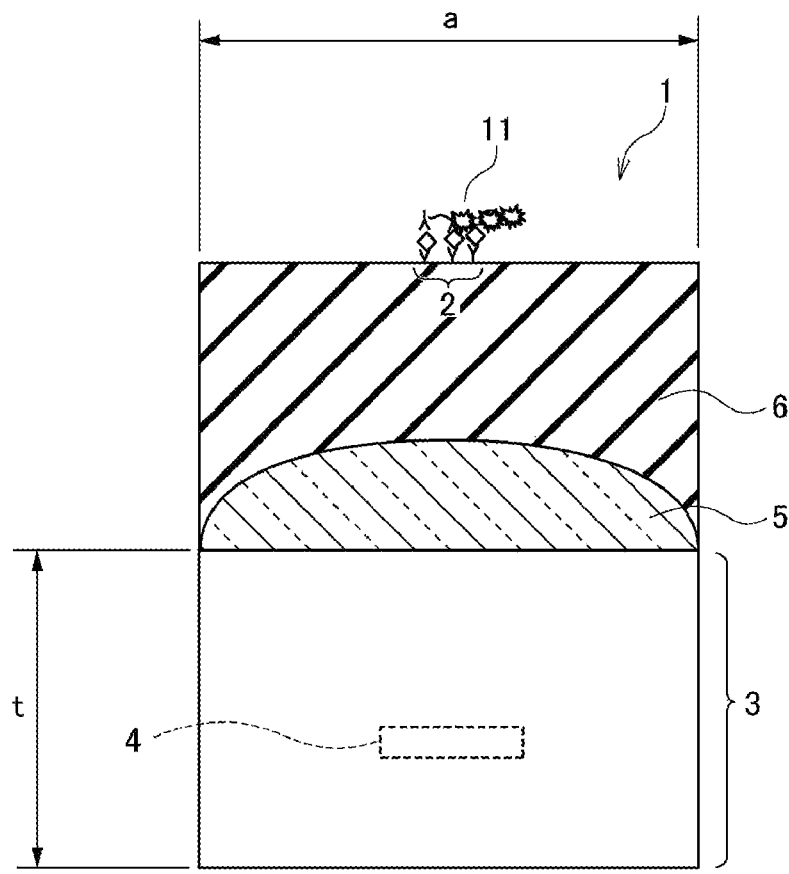
[FIG. 2]

First, an image sensor according to a first embodiment of the present disclosure will be described. FIG. 1 is a plan view schematically showing a structure of the image sensor of this embodiment. FIG. 2 is a cross-sectional diagram showing a structure of a pixel cell 1.

(Overall Structure)

As shown in FIGS. 1 and 2, in the image sensor 10 of this embodiment, a plurality of macro-lenses 5 are arranged on a photoelectric conversion unit 3 on which a plurality of light-receiving devices constituting a pixel cell 1 are arranged in a matrix. An insulation layer 6 is formed to cover the macro-lenses 5, and a detection area 2 is provided for each pixel cell 1 on the insulation layer 6.

(Photoelectric Conversion Unit 3)

The photoelectric conversion unit 3 is a portion that detects an optical phenomenon such as a luminescence process in a sample 11 by the light-receiving devices and outputs it as an electric signal. For example, when using a solid-state image pickup device such as a CCD and a CMOS, the light-receiving devices are structured by PN bonding. Moreover, a size a of each pixel cell 1 of the photoelectric conversion unit 3 is not particularly limited and can be set to be, for example, 0.2 to 10 μm square. Further, a thickness t of the photoelectric conversion unit 3 is also not particularly limited and can be set to be about 1 to 10 μm as in the image sensor of the related art.

(Macro-lens 5)

The macro-lenses 5 collect light toward a light-receiving unit of the light-receiving devices arranged in the photoelectric conversion unit 3 and are arranged in an immediately-above area of the light-receiving devices for each pixel cell 1. In the image sensor 10 of this embodiment, a single macro-lens may be provided with respect to a single light-receiving device, or a plurality of light-receiving devices may be provided with respect to a single macro-lens. Moreover, the shape of the macro-lens 5 is not particularly limited, and lenses of various shapes such as a plane-convex lens and a biconvex lens are applicable. An array method is also not particularly limited and can be selected as appropriate.

Figure 3:
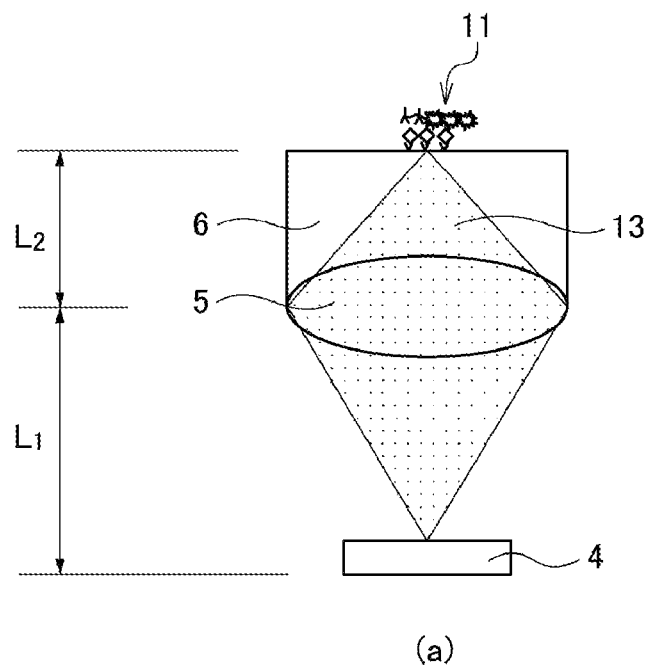
[FIG. 3]
Figure 3:
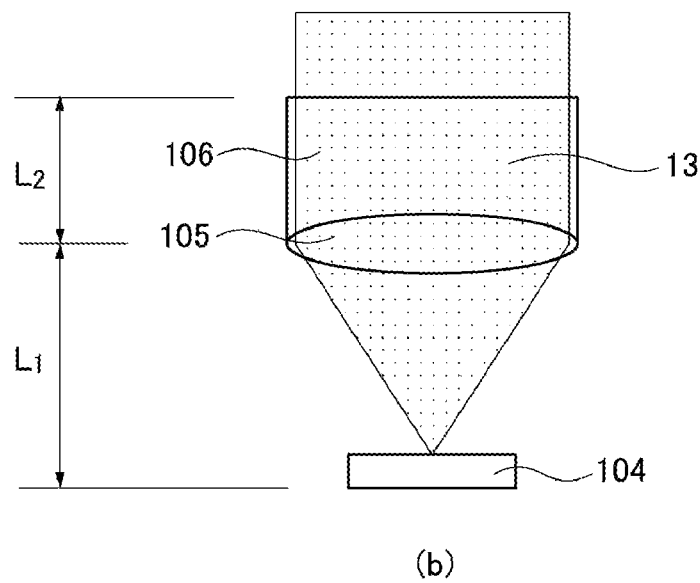
Figure 4:
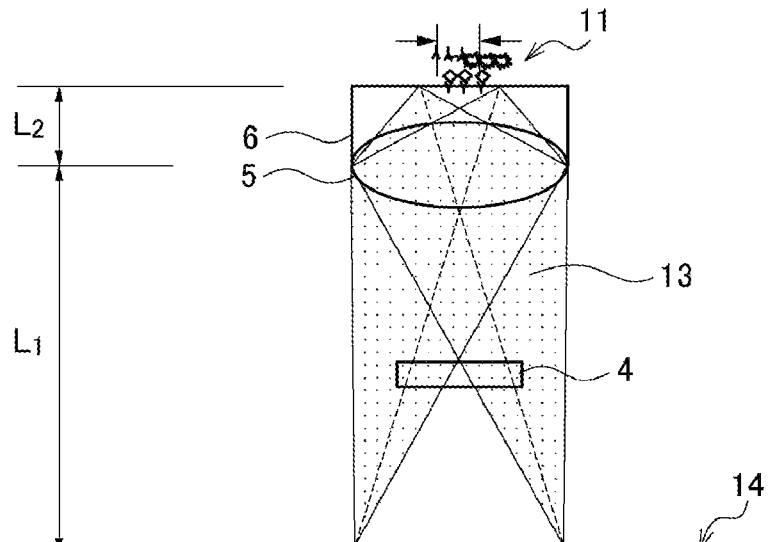
[FIG. 4]
Figure 4:
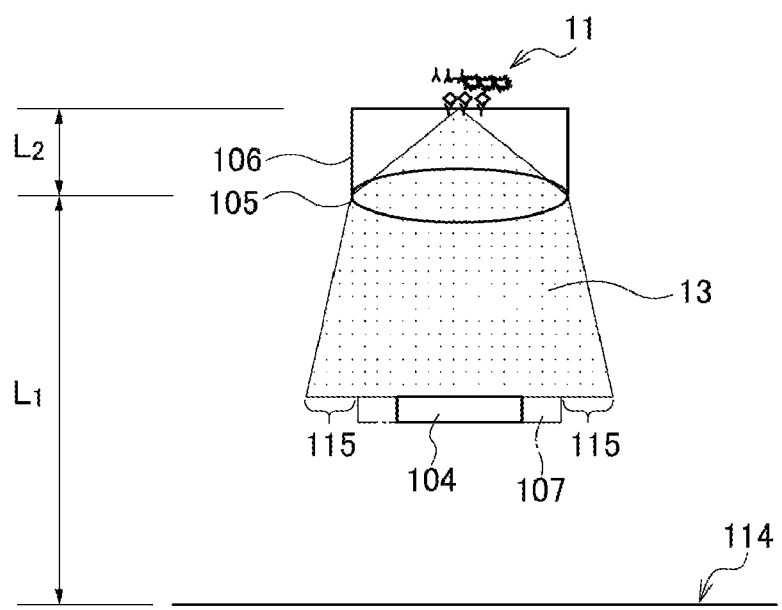
Figure 5:
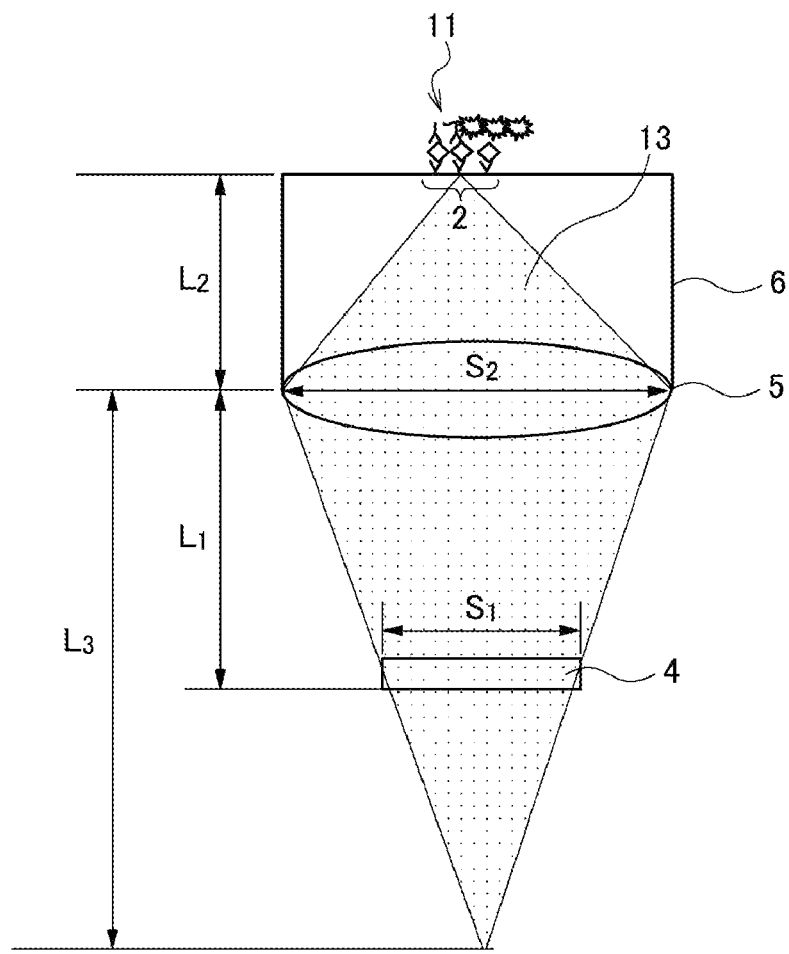
[FIG. 5]

FIG. 3(a) is a diagram showing a light collection state in the image sensor 10 of this embodiment, and FIG. 3(b) is a diagram showing a light collection state of an image sensor of the related art. Further, FIG. 4(a) is a diagram showing a focal point formation of a macro-lens 5, and FIG. 4(b) is a diagram showing a state when measured by the image sensor of the related art. Furthermore, FIG. 5 is a diagram showing a favorable condition of a focal distance f of the macro-lens 5. It should be noted that in FIGS. 3 to 5, for brevity of the figures, constituent elements between the light-receiving unit 4 and the macro-lens 5 are omitted, and the macro-lens 5 is described as a biconvex lens.

As shown in FIG. 3(*b*), the image sensor of the related art normally takes a structure of collecting parallel light on a light-receiving surface. Therefore, when a refractive index from a macro-lens 105 to a light-receiving unit 104 as the light-receiving surface is represented by $n_1$ and a distance from the lens 105 to an imaging surface is represented by $L_1$, a focal distance f of the macro-lens 105 becomes $f \geq L_1 * n_1$. Therefore, as shown in FIG. 4(*b*), in the case of the image sensor structure of the related art, even if the sample 11 is fixed to a pixel center portion, the distance $L_1$ from the macro-lens 105 to the imaging surface becomes a negative value, thus resulting in a system that does not collect light.

On the other hand, as shown in FIGS. 3(*a*) and 4(*b*), in the image sensor 10 of this embodiment, a focal point of the macro-lens 5 is formed such that a light flux that is emitted from the detection area 2 and is at least in midst of being collected becomes parallel or is converged and accommodated in the corresponding light-receiving unit 4. Specifically, the thickness of the insulation layer 6, the distance from the macro-lens 5 to the light-receiving unit 4, the sizes of the light-receiving device and light-receiving unit 4, and the like are adjusted such that the focal distance f of the macro-lens 5 becomes $f < L_2 * n_2$. Here, $n_2$ represents a refractive index of the insulation layer 6, and $L_2$ represents a distance from the sample 11 to the macro-lens 5.

Further, it is favorable for the focal distance f of the macro-lens 5 to be set under the condition that all of the light from the detection area 2 geometrically enters the light-receiving unit 4 as shown in FIG. 5. Specifically, when the detection area 2 exists only in the vicinity of an optical axis of the macro-lens 5, the condition under which the entire light speed emitted from the macro-lens 5 having a diameter $S_2$ enters the light-receiving unit 4 having a diameter $S_1$ is geometrically expressed by Mathematical Expression (1) below. Here, $L_1$ in Mathematical Expression (1) below represents a distance from the macro-lens 5 to the light-receiving unit 4, and $L_3$ represents a distance from the macro-lens 5 to the focal point.

[Math. 1]

$$\frac{S_2}{L_3} = \frac{S_1}{(L_3 - L_1)} \quad (1)$$

Dissolving Mathematical Expression (1) above regarding $L_3$, Mathematical Expression (2) below can be obtained.

[Math. 2]

$$L_3 = \frac{L_1 \times S_2}{(S_2 - S_1)} \quad (2)$$

Furthermore, for focusing light from the detection area 2 more in the front than $L_3$ expressed by Mathematical Expression (2) above, the focal distance f of the macro-lens 5 only needs to satisfy Mathematical Expression (3) below. Here, $n_1$ in Mathematical Expression (3) below represents a refractive index from the macro-lens 5 to the light-receiving unit 4, and n2 represents a refractive index of the insulation layer 6.

[Math. 3]

$$f \leq \frac{L_1 \times L_2 \times n_1 \times n_2 \times S_2}{L_1 \times n_1 \times S_2 + L_2 \times n_2 \times (-S_1 + S_2)} \quad (3)$$

It should be noted that it is ideal for the focal distance f of the macro-lens 5 to satisfy Mathematical Expression (4) below.

[Math. 4]

$$\frac{1}{f} = \frac{1}{(L_1 \times n_1)} + \frac{1}{(L_2 \times n_2)} \quad (4)$$

(Insulation Layer 6)

The insulation layer 6 is provided for protection of the photoelectric conversion unit 3, electrical insulation of the light-receiving devices and peripheral integrated circuits, structural support, surface flattening, and the like and is formed of a material that transmits light and does not affect a light detection in the sample 11 and the light-receiving devices. Specifically, the insulation layer 6 can be formed of an inorganic material having optical transparency, such as oxide silicon and silicon nitride ($SiN_x$), or a high-polymer material having a high melting point and optical transparency, such as polyimide.

Further, a material that transmits only detection target wavelength light such as fluorescent light and absorb or reflect light that is not the detection target, such as excitation light, may be used. Furthermore, when the insulation layer 6 is formed of a transparent material, it is desirable to provide a color filter that transmits only detection target wavelength light and absorbs light that is not the detection target between the macro-lens 5 and the light-receiving unit 4. It should be noted that the thickness of the insulation layer 6 is not particularly limited and only needs to be enough to flatten the surface, but from the relationship with the focal distance f of the lens, the thickness is favorably about 1 to 30 μm.

(Detection Area 2)

The detection areas 2 are provided for each of the light-receiving devices on the surface of the insulation layer 6 while being apart from one another. Moreover, the center of the detection area 2 is positioned on an extended line connecting the center of the light-receiving unit 4 of each light-receiving device and the center of the lens 5 located right above the light-receiving device. In the image sensor 10 of this embodiment, the sample 11 is fixed to only the detection area 2, and only the light emission in this portion is detected in the light-receiving unit 4. Here, a ratio of the detection area 2 to the pixel cell 1 can be set as appropriate based on the size of the light-receiving surface of the light-receiving device and the like, but from a viewpoint of a crosstalk suppression, the ratio is favorably about 1 to 70%.

A method of fixing the sample 11 is not particularly limited, but it is possible to carry out surface processing such as hydrophobic processing and hydrophilic processing on the detection area 2 and fix the sample 11 to only that portion. Further, it is also possible to fix an antibody, an adapter, a gene-adsorptive material, and the like that couple with the sample 11 to the detection area 2 in advance by various printing methods such as an inkjet method and couple the sample 11 to them to fix the sample 11.

(Production Method)

Next, a production method for the image sensor 10 structured as described above will be described. When producing the image sensor 10 of this embodiment, a photoelectric conversion unit 3 that includes a plurality of light-receiving devices and converts incident light into an electric signal is first formed on a semiconductor wafer. Next, in an immediately-above area of the light-receiving devices, a plurality of macro-lenses 5 that collect light toward the light-receiving units 4 of the light-receiving devices positioned right below the lenses are formed, and an insulation layer 6 formed of an optically-transparent material is additionally formed above the lenses. The method of forming the photoelectric conversion unit 3, the macro-lenses 5, and the insulation layer 6 is not particularly limited, and various known methods are applicable.

Next, on the surface of the insulation layer 6, the detection areas 2 to which a sample as a detection target is fixed are formed for each of the light-receiving devices while being apart from one another, a center of the detection area 2 being positioned on an extended line connecting the center of the light-receiving unit 4 of each light-receiving device and the center of the lens positioned right above the light-receiving device. At this time, it is possible to carry out surface processing such as hydrophobic processing and hydrophilic processing on the detection area 2 or fix an antibody, an adapter, a gene-adsorptive material, and the like that couple with the sample 11 by various printing methods, for example. As a result, the sample 11 can be easily fixed to only the detection area 2. After that, the wafer is cut by a known method and separated into individual image sensors 10.

(Operation)

Figure 6:
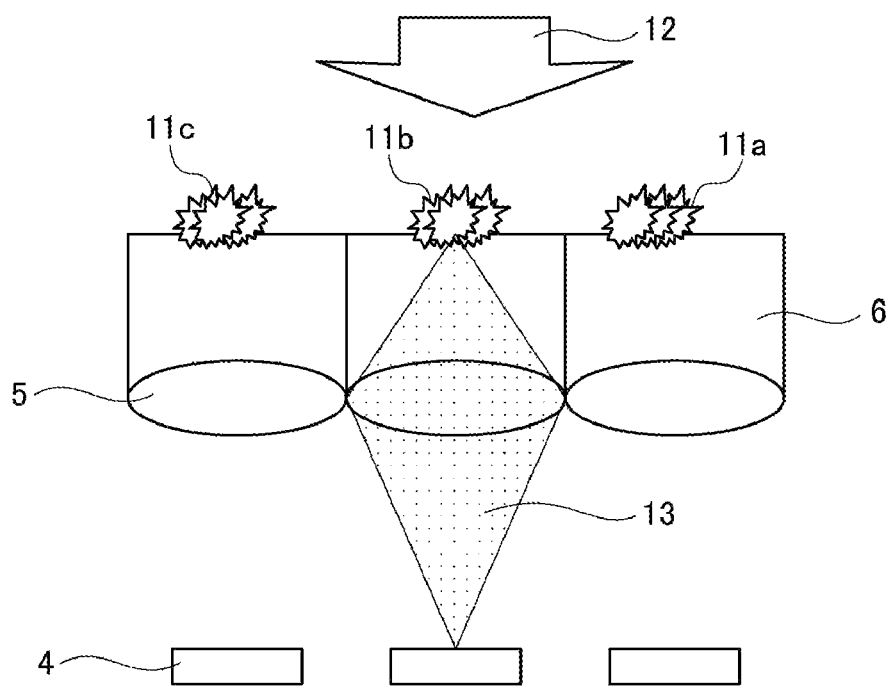
[FIG. 6]
Figure 7:
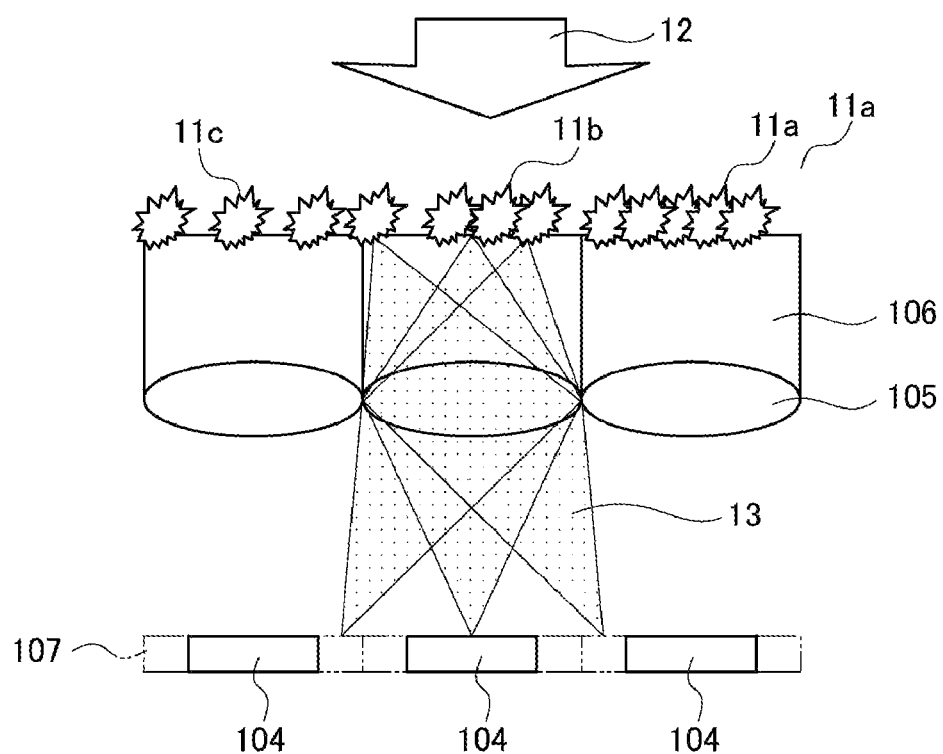
[FIG. 7]

Next, an operation of the image sensor 10 of this embodiment will be described while taking a case of measuring a luminescence process of a sample modified by a fluorescent pigment as an example. FIG. 6 is a diagram schematically showing a measurement state of the image sensor 10, and FIG. 7 is a diagram schematically showing a measurement state when the detection area 2 is not limited to a pixel center portion. It should be noted that in FIGS. 6 and 7, for brevity of the figures, constituent elements between the light-receiving unit 4 and the macro-lens 5 are omitted, and the macro-lens 5 is described as a biconvex lens.

As shown in FIG. 6, in the image sensor 10 of this embodiment, excitation light 12 is irradiated onto samples 11a to 11c fixed to the detection areas 2. Accordingly, fluorescent light corresponding to the samples 11a to 11c is generated. In the case of the sample 11b, for example, fluorescent light 13 generated by the excitation light 12 enters the insulation layer 6, is collected by the macro-lens 5, and enters the light-receiving unit 4 of the light-receiving device.

At this time, in the image sensor 10 of this embodiment, the center of the detection area 2 is positioned on the extended line connecting the center of the macro-lens 5 and the center of the light-receiving unit 4 (optical axis), and a light emission occurs only in the vicinity of that portion. As a result, the fluorescent light 13 emitted from the sample 11b can be efficiently collected by the macro-lens 5, and thus a detection sensitivity is improved. Moreover, the image sensor 10 can prevent crosstalk in which fluorescent light emitted from other samples 11a and 11c enters other light-receiving units 4 from occurring.

In contrast, since the samples 11a to 11c are fixed to the entire surface of the pixel cells 1 in the image sensor of the related art shown in FIG. 7, the fluorescent light 13 emitted from the sample 11b by the irradiation of the excitation light 12 is collected in the light-receiving unit 4 of the same pixel cell 1 and also enters other adjacent light-receiving units 4. In other words, crosstalk occurs among adjacent pixels.

As described above in detail, in the image sensor 10 of this embodiment, since the samples 11 are fixed to only the detection areas 2 whose center is positioned on the extended line of the optical axis of the macro-lens 5 while being apart from one another for each of the light-receiving devices, light collection efficiency can be improved, and stray light can be prevented from traveling to adjacent pixels.

<2. Second Embodiment>

Figure 8:
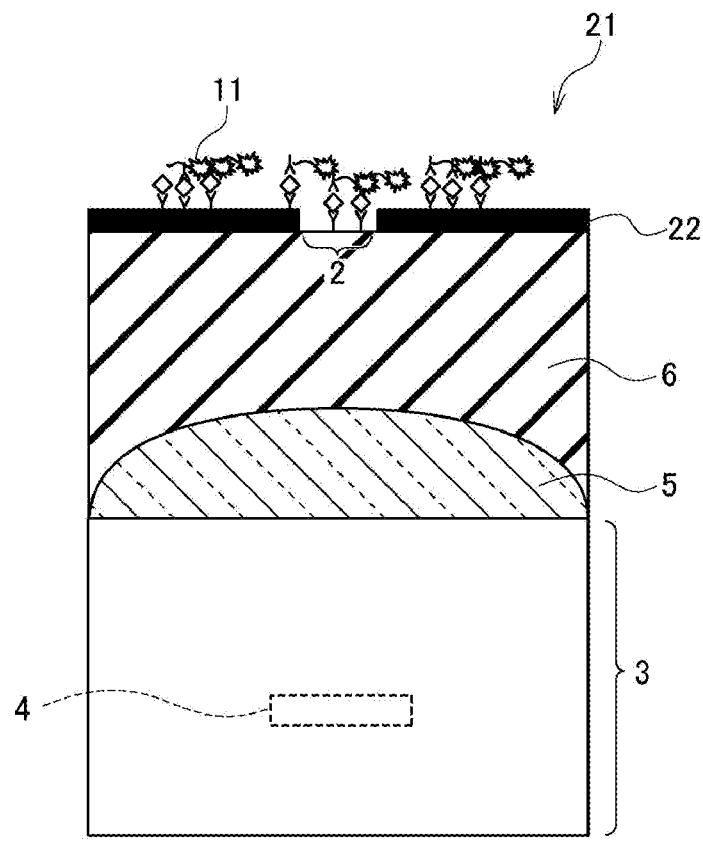
[FIG. 8]

Next, an image sensor according to a second embodiment of the present disclosure will be described. FIG. 8 is a cross-sectional diagram showing a structure of a pixel cell of the image sensor of this embodiment. It should be noted that in FIG. 8, constituent elements that are the same as those of the pixel cell 1 of the image sensor according to the first embodiment shown in FIG. 2 are denoted by the same symbols, and detailed descriptions thereof will be omitted.

(Overall Structure)

As shown in FIG. 8, in the image sensor of this embodiment, a light shield mask 22 that shields light is formed in a portion excluding the detection area 2 on the surface of the insulation layer 6.

(Light Shield Mask 22)

The material of the light shield mask 22 is not particularly limited as long as it absorbs and/or reflects light such as the excitation light 12 and the fluorescent light 13 emitted from the sample 11, but can be formed using, for example, an aluminum thin film, a chrome oxide thin film, and a light-sensitive resin. Moreover, the formation method is also not particularly limited, and known methods such as dry etching and optical lithography are applicable.

(Operation)

In the image sensor of this embodiment, nucleuses can be formed at random at a density with which a nucleus that may cause a luminescence process is incorporated about one each into a non-light-shield portion (detection area 2) of a pixel cell 21. Moreover, in the image sensor of this embodiment, the sample 11 may be fixed to portions other than the detection area 2. Therefore, the sample 11 or an antibody, an adapter, or a gene-adsorptive material that couples with the sample 11 may be fixed to the surface of the pixel cell 21 by performing printing or the like with lower accuracy from above the light shield mask 22, for example.

As described above in detail, in the image sensor of this embodiment, since the light shield mask 22 is formed in a portion excluding the detection area 2, even when the sample 11 is fixed to the entire surface of the pixel cell 21, stray light can be prevented from traveling to adjacent pixels. It should be noted that structures and effects of the image sensor of this embodiment other than those described above are the same as those of the first embodiment described above.

<2. Third Embodiment>

Figure 9:
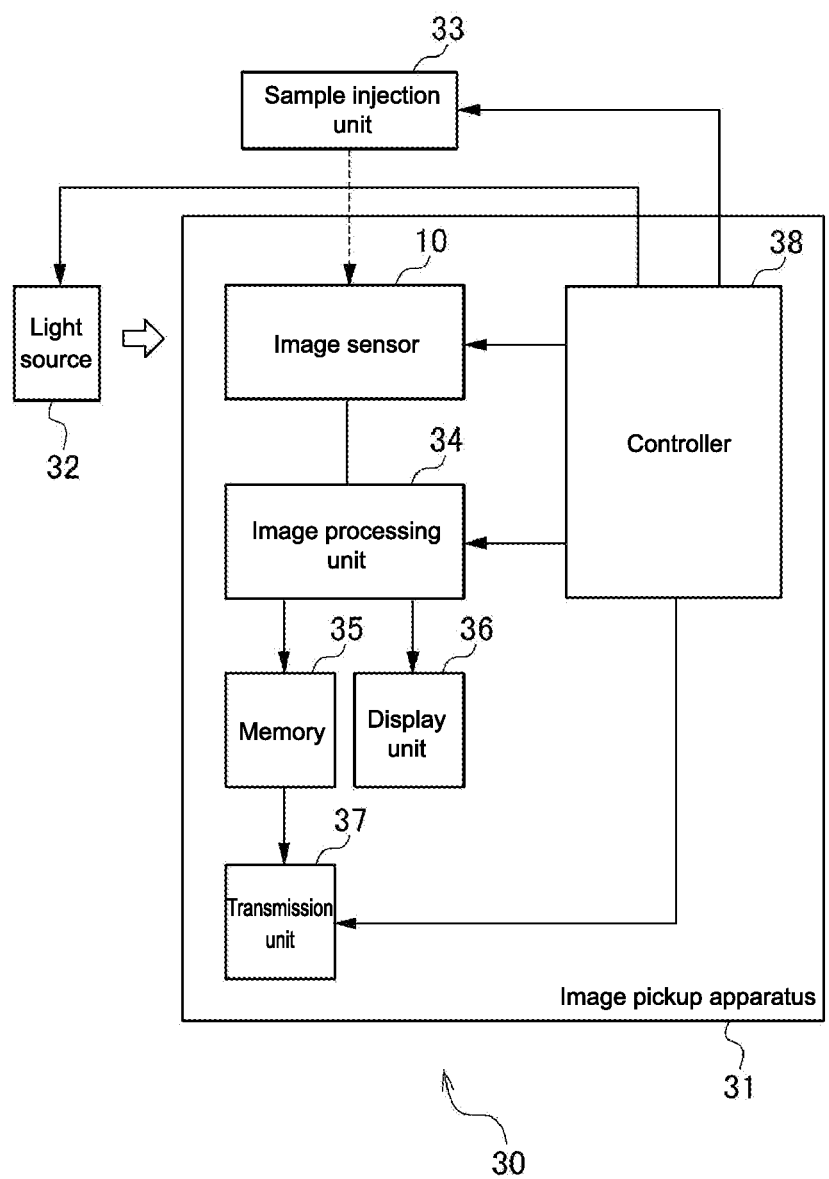
[FIG. 9]

Next, an inspection apparatus according to a third embodiment of the present disclosure will be described. FIG. 9 is a block diagram showing a structure of the inspection apparatus of this embodiment. As shown in FIG. 9, the image sensor 10 according to the first embodiment described above is mounted on the inspection apparatus 30 of this embodiment, and by irradiating light emitted from a light source 32 onto a sample 11 injected from a sample injection unit 33, for example, a luminescence process thereof is detected.

An image pickup apparatus 31 of the inspection apparatus 30 includes, in addition to the image sensor 10, an image processing unit 34 that processes a detection signal, a memory 35 that stores processed data, a display unit 36 as a display, and a transmission unit 37 that transmits data in the memory 35. The image pickup apparatus 31 also includes a controller 38 that controls the image sensor 10, the image processing unit 34, the transmission unit 37, the light source 32, and the sample injection unit 33.

Since the image sensor 10 in which traveling of stray light to adjacent pixels is suppressed is mounted on the inspection apparatus 30 of this embodiment, a luminescence process of a sample can be detected accurately. It should be noted that although the case where the image sensor 10 is mounted is taken as an example in this embodiment, the present disclosure is not limited thereto, and the same effect can be obtained even when the image sensor of the second embodiment is mounted.

Further, the present disclosure may also take the following structures.

(1)

An image sensor, including:

a light source conversion unit that includes a plurality of light-receiving devices and converts incident light into an electric signal;

a plurality of lenses that are provided in an immediately-above area of the light-receiving devices and collect light toward a light-receiving unit of the light-receiving devices positioned right below the lenses;

an insulation layer that is formed of an optically-transparent material and formed above the lenses; and detection areas that are provided on a surface of the insulation layer while being apart from one another for each of the light-receiving devices, a center of each of the detection areas being positioned on an extended line connecting a center of the light-receiving unit of each of the light-receiving devices and a center of the lens provided right above each of the light-receiving devices, a sample as a detection target being fixed to at least the detection areas.

(2)

The image sensor according to (1), in which, when a refractive index of the insulation layer is represented by n and a distance between the sample and the lens is represented by L, a focal distance f of the lens is shorter than an optical path length (=n*L) between the sample and the lens.

(3)

The image sensor according to (1) or (2), in which the sample as the detection target is fixed to only the detection areas.

(4)

The image sensor according to (3), in which the detection areas are subjected to surface processing.

(5)

The image sensor according to (3), in which the detection areas have an antibody, an adapter, or a gene-adsorptive material fixed thereto.

(6)

The image sensor according to any one of (1) to (5), in which the surface of the insulation layer have a light shield mask formed on a portion excluding the detection areas.

(7)

The image sensor according to any one of (1) to (6), in which the insulation layer is formed of silicon oxide.

(8)

A production method for an image sensor, including the steps of:

forming, on a semiconductor wafer, a photoelectric conversion unit that includes a plurality of light-receiving devices and converts incident light into an electric signal;

forming, in an immediately-above area of the light-receiving devices, a plurality of lenses that collect light toward a light-receiving unit of the light-receiving devices positioned right below the lenses;

forming, above the lenses, an insulation layer that is formed of an optically-transparent material; and forming, on a surface of the insulation layer while being apart from one another for each of the light-receiving devices, detection areas whose center is positioned on an extended line connecting a center of the light-receiving unit of each of the light-receiving devices and a center of the lens provided right above each of the light-receiving devices.

(9)

An inspection apparatus, including the image sensor according to any one of (1) to (7).

Reference Signs List 1, 21 pixel cell
2 detection area
3 photoelectric conversion unit
4, 104 light-receiving unit
5, 105 macro-lens
6 insulation layer
10 image sensor
11, 11a to 11c sample
12 excitation light
13 fluorescent light
a size of pixel cell 1
t thickness of photoelectric conversion unit 3
30 inspection apparatus
31 image pickup apparatus
32 light source 32
33 sample injection unit
34 image processing unit
35 memory
36 display unit
37 transmission unit
38 controller

The invention claimed is:

1. An image sensor comprising:

an insulation layer that is optically-transparent, a first surface of the insulation layer is between a lens and a second surface of the insulation layer; and a light-receiving unit that is located at an imaging surface, the lens is between the light-receiving unit and the first surface of the insulation layer, wherein the lens has a focal distance that satisfies a structural relationship of $$1/f = 1/(L_1 \times n_1) + 1/(L_2 \times n_2), \text{ with}$$

"f" being the focal distance of the lens,

"$L_1$" being a distance from the lens to the imaging surface,

"$n_1$" being a refractive index from the lens to the light-receiving unit,

"$L_2$" being a distance from the second surface to the lens, and

"$n_2$" being a refractive index of the insulation layer.

2. The image sensor according to claim 1, wherein the second surface of the insulation layer has a detection area, a sample is fixed to the detection area.

3. The image sensor according to claim 2, wherein the focal distance of the lens is shorter than an optical path length, the optical path length is another structural relationship that satisfies $$OPL = (n_2 \times L_{OPL}), \text{ with}$$

"OPL" being the optical path length,
"$n_2$" being the refractive index of the insulation layer, and
"$L_{OPL}$" being a distance between the sample and the lens.

4. The image sensor according to claim 1, wherein the lens is a plane-convex lens.

5. The image sensor according to claim 1, wherein the lens is a biconvex lens.

6. The image sensor according to claim 1, wherein the insulation layer touches the lens.

7. The image sensor according to claim 1, wherein the light-receiving unit is configured to convert incident light into an electric signal.

8. The image sensor according to claim 7, wherein the incident light on the light-receiving unit is transmissible through the insulation layer and the lens.

9. The image sensor according to claim 1, wherein an antibody, an adapter, or a gene-adsorptive material is fixed the insulation layer.

10. The image sensor according to claim 1, further comprising:
a light shield mask on the second surface of the insulation layer, the lens is between the light-receiving unit and an opening through the light shield mask.

11. The image sensor according to claim 1, wherein the insulation layer is an inorganic material.

12. The image sensor according to claim 1, wherein the insulation layer is silicon oxide.

13. The image sensor according to claim 1, wherein the insulation layer is silicon nitride.

14. The image sensor according to claim 1, wherein the insulation layer is a high-polymer material.

15. The image sensor according to claim 1, wherein the insulation layer is a polyimide.

16. An inspection apparatus comprising:
the image sensor according to claim 1.

17. A production method for an image sensor comprising:
forming a photoelectric conversion unit on a semiconductor wafer, the photoelectric conversion unit includes light-receiving units;
forming lenses above the light-receiving units, one of the light-receiving units is located at an imaging surface;
forming an optically-transparent insulation layer above the lenses, a first surface of the insulation layer is between the lenses and a second surface of the insulation layer; and
spacing the insulation layer, the imaging surface, one of the lenses, and said one of the light-receiving units to have a structural relationship that satisfies $1/f = 1/(L_1 \times n_1) + 1/(L_2 \times n_2)$, with
"f" is a focal distance of said one of the lenses,
"$L_1$" is a distance from said one of the lenses to the imaging surface,
"$n_1$" is a refractive index from said one of the lenses to said one of the light-receiving units,
"$L_2$" is a distance from the second surface to said one of the lenses, and
"$n_2$" is a refractive index of the insulation layer,
wherein said one of the lenses is between the first surface of the insulation layer and said one of the light-receiving units.

18. The method according to claim 17, further comprising:
fixing a sample is fixed to a detection area, the detection area is a portion of the second surface of the insulation layer.

19. The method according to claim 18, wherein distance of said one of the lenses is shorter than an optical path length, the optical path length is a structural relationship that satisfies $OPL = (n_2 \times L_{OPL})$, with
"OPL" being the optical path length,
"$n_2$" being the refractive index of the insulation layer, and
"$L_{OPL}$" being a distance between the sample and said one of the lenses.

20. The method according to claim 17, further comprising:
forming a light shield mask on the second surface of the insulation layer, said one of the lenses is between said one of the light-receiving units and an opening through the light shield mask.

* * * * *